United States Patent [19]

Kürzinger

[11] Patent Number: 5,158,894

[45] Date of Patent: Oct. 27, 1992

[54] METHOD FOR DETERMINING THE CARBONATE CONTENT OF WASHING SUSPENSIONS

[75] Inventor: Karl Kürzinger, Helmstadt, Fed. Rep. of Germany

[73] Assignee: KRC Umwelttechnik GmbH, Wurzburg, Fed. Rep. of Germany

[21] Appl. No.: 603,368

[22] Filed: Oct. 26, 1990

[30] Foreign Application Priority Data

Oct. 27, 1989 [DE] Fed. Rep. of Germany ....... 3935720

[51] Int. Cl.$^5$ ...................... G01N 33/00; C01B 17/00
[52] U.S. Cl. ...................... 436/133; 436/50; 436/128; 436/145; 436/171; 436/175; 436/181; 423/243.07; 423/243.01
[58] Field of Search .......... 423/242 A, 242 R, 244 A, 423/244 R; 436/50, 128, 133, 145, 171, 175, 181; 422/261

[56] References Cited

U.S. PATENT DOCUMENTS

| | | | |
|---|---|---|---|
| 961,763 | 6/1910 | Falding | 423/242 R |
| 3,672,841 | 6/1972 | Freeman et al. | |
| 4,035,470 | 7/1977 | Senjo et al. | 423/242 A |
| 4,061,743 | 12/1977 | Senjo et al. | 423/242 A |
| 4,397,957 | 8/1983 | Allison | |
| 4,663,724 | 5/1987 | Onizuka et al. | 436/133 |
| 4,677,077 | 6/1987 | Onizuka et al. | 436/133 |
| 4,683,210 | 7/1987 | Onizuka et al. | 436/133 |
| 4,683,211 | 7/1987 | Onizuka et al. | 436/133 |
| 4,698,314 | 10/1987 | Tao | 436/181 |

FOREIGN PATENT DOCUMENTS

| | | | |
|---|---|---|---|
| 89/12699 | 12/1989 | PCT Int'l Appl. | |
| 1346974A | 10/1987 | U.S.S.R. | 436/133 |
| 2135455 | 8/1984 | United Kingdom | |
| 2135455A | 8/1984 | United Kingdom | 436/133 |

*Primary Examiner*—James C. Housel
*Assistant Examiner*—Maureen Wallenhorst
*Attorney, Agent, or Firm*—Wegner, Cantor, Mueller & Player

[57] ABSTRACT

A method for determining the carbonate content of washing suspensions of flue gas desulfurization plants using limestone is carried out by first admixing the samples, being at a temperature of from 40° C. to 70° C., with an excess amount relative to the maximum possible sulfite content, of an iron(III) chloride solution for the oxidation of the sulfite to sulfate, and then by addition of an excess amount of sulfuric acid or another acid, measuring the amount of escaping gas corresponding to the carbonate content.

6 Claims, No Drawings

METHOD FOR DETERMINING THE CARBONATE CONTENT OF WASHING SUSPENSIONS

The present invention relates to a method for determining the carbonate content of washing suspensions of flue gas desulfurization plants using limestone. Said suspensions generally contain gypsum, sulfite, chloride and carbonate as the major components. If such a suspension is acidified to become strongly acidic $SO_2$ from the sulfite will be released in addition to $CO_2$. Thus, the amount of gas released corresponds to the sum of carbonate content plus sulfite content. In order to prevent the release of $SO_2$ it is basically possible to previously oxidize the sulfite to form sulfate. However, for this purpose only oxidizing agents can be employed which do not release gases themselves or do not form gases with the remaining components of the suspension. Thus, for example, strong oxidants such as permanganate are capable of oxidizing chloride to chlorine and thereby producing another interfering gaseous component.

The determination of carbonate in such suspensions is of interest, inter alia, because, on the one hand, a sufficient amount of carbonate must be present in order to bind the $SO_2$ from the flue gases and, thus, to stabilize the pH value of the washing suspensions. On the other hand, too high carbonate concentrations lead to undesirable carbonate content of the resulting flue gas gypsum. An amount of carbonate which is too high will in turn damage or prevent the subsequent processability of flue gas gypsum.

Hence, it is the object of the invention, in any easy and reliable manner and without much delay in time to determine the carbonate content in washing suspensions of flue gas desulfurization plants employing limestone. In such a procedure the sulfite and any possibly dissolved $SO_2$ will have to be removed, preferably by way of an oxidation to sulfate. However, the oxidizing agent to be employed must not be so strong as to also oxidize the chloride, which is always present in these washings, to form chlorine which would adversely affect the results of the measurement.

Said object can be attained in a surprisingly simple manner by first admixing the samples, being at a temperature of from 40° C. to 70° C., with an excess amount, relative to the maximum possible sulfite content, of an iron(III) chloride solution for oxidation of the sulfite to sulfate, and then by means of addition of an excess amount of sulfuric acid or some other acid, measuring the amount of escaping gas corresponding to the carbonate content.

The amount of escaping gas may be measured, for example, by measuring the volume of the displaced liquid such as a diluted acid. It is necessary that the water be acidified, because otherwise the $CO_2$ formed will be dissolved in the neutral water to an unacceptably high degree such as to produce false results of the measurement. The diluted acids may especially include diluted hydrochloric acid or diluted sulfuric acid. Apart from acidified water, inorganic and/or organic liquids which virtually do not absorb any $CO_2$ may also be considered.

A further possibility consists of measuring the amount of released gas by way of measuring the increase in pressure in a closed vessel. In either method, of course, care must be taken that the temperature is sufficiently constant, since otherwise the results of the measurement may be subject to considerable error. More specifically, if the pressure increase in a closed vessel is to be measured, calibration curves are first established by employing samples having known compositions. Nevertheless, it is the advantage of such measurements that they can be more readily carried out by semi-skilled staff. Even if said methods of measurement involve deviations of $\pm 5\%$, this will be sufficient for the above-mentioned purpose of the carbonate determination. It is just crucial that the carbonate content fluctuate within some given limits such as, on the one hand, to ensure a sufficient desulfurization and, on the other hand, to obtain a low-carbonate flue gas gypsum.

Test series measuring solutions having known carbonate contents and containing increasing amounts of sulfite and chloride have shown that in the method according to the invention virtually always the same and true results are found. Thus, the results of the measurements have been affected or falsified by neither sulfite nor chloride.

Finally, it will also be possible to determine the amount of escaping gas and/or the $CO_2$ concentration thereof by means of physical, physicochemical or chemical methods. These include, for example, infrared or ultraviolet measurements or the use of miniature gas flow meters.

In principle, it is quite possible in a second step in the same apparatus to determine the amount of gas escaping without the addition of iron(III) chloride solution. Then the sum of sulfite and carbonate will be obtained. Thus, upon subtraction of the value representing the amount of carbonate alone, it is also feasible to determine the sulfite content in a simple manner. This parameter may be also of interest in order to monitor the successful operation and the efficiency of the flue gas desulfurization. More particularly, the sulfite content is of interest if the plant is operated under changing loads and the flue gas desulfurization units are to be adapted to the changed situations.

EXAMPLE

Two samples with increasing amounts of limestone (calcium carbonate) between 7.5 to 45 g/l were added to 100 ml of a solution of $FeCl_3.6H_2O$ (containing 620 g/l). The temperature was 50° C. and the volume was 330 ml. Few minutes later 20 ml of sulfuric acid (50%) were added under stirring. The volume of the liberated gas was measured The resulting volumes were plotted in a diagramm and gave a straight line.

The experiments were repeated, however, increasing amounts of calcium sulfite ($CaSO_3 \times 0.5\ H_2O$ of 5 g, 10 g and 15 g). Furtheron up to 30,000 ppm chloride were added in form of calcium chloride. The amounts of gas liberated were substantially the same and were all on the same straight line.

I claim:

1. A process for determining the carbonate content of a washing suspension of flue gas desulfurization plants employing limestone, said process comprising:
   (a) admixing samples of said washing suspension containing sulfite and a carbonate at a temperature of 40° C. to 70° C. with an excess amount of an iron(III) chloride solution to oxidize the sulfite to sulfate, said excess amount of the iron(III) chloride solution being relative to a predetermined maximum sulfite content of said washing suspension;
   (b) adding an acid to the admixture obtained in step (a) to convert the carbonate to $CO_2$ gas;

(c) measuring the amount of gas escaping from the admixture obtained in step (b); and (d) determining the carbonate content of said samples from the measurements obtained in step (c).

2. The process according to claim 1, wherein the acid is sulfuric acid.

3. The process according to claim 1, wherein the amount of escaping gas is measured by determining a volume of liquid displaced by the escaping gas from the admixture obtained in step (b).

4. The process according to claim 1, wherein the amount of escaping gas is measured with a gas flow meter.

5. The process according to claim 1, wherein the amount of escaping gas is measured by infrared or ultraviolet measurement.

6. The process according to claim 1, wherein step (b) is carried out in a closed vessel, and the amount of escaping gas is measured by determining the increase in pressure in the closed vessel.

* * * * *